Nov. 8, 1932. W. G. SUTHERLAND Plant Pat. 40
THORNLESS BARBERRY
Filed May 7, 1932
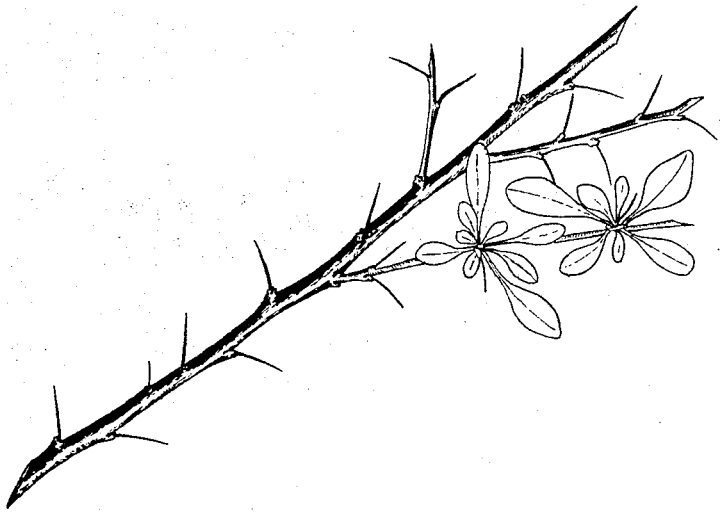
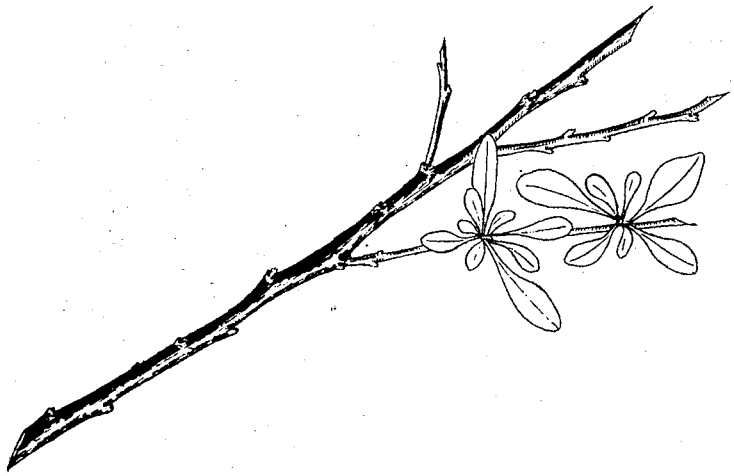
Inventor:
W. G. Sutherland
By Robb & Robb,
Attorneys Patented Nov. 8, 1932

Plant Pat. 40

UNITED STATES PATENT OFFICE

WILLIAM GORDON SUTHERLAND, OF BOULDER, COLORADO, ASSIGNOR TO STARK BRO'S NURSERIES & ORCHARDS COMPANY, OF LOUISIANA, MISSOURI

THORNLESS BARBERRY

Application filed May 7, 1932. Serial No. 609,897.

My invention relates to a new thornless barberry of the *Berberis thunbergii* type, the novelty residing primarily in the absence of spines or thorns. In other respects the new variety closely resembles the *Berberis thunbergii* with the exception that the coloring of the leaves is somewhat distinct.

The *Berberis thunbergii* is a dense, low shrub which is very valuable for borders of walks and drives and for low ornamental hedges. Its horizontal growth characteristic, hardiness, large brilliant red fruits remaining fresh until the following spring season, ability to endure partial shade, and bright scarlet fall coloring greatly enhance its value for these purposes. Owing to the abundance of spines or needle-like thorns for which this variety is noted, there is considerable demand for this plant for use for evergreen protection and as a bramble. However, there is also a great demand for foundation and group plantings where brambles are undesirable or unnecessary, and my new variety of thornless barberry is excellently adapted for these purposes.

Heretofore it has been impracticable to plant the *Berberis thunbergii* very close to a walk because of its destructive spines or brambles which catch and tear the clothing and/or flesh of a passerby. Likewise, placing these plants too close to a driveway results in scratching or otherwise marring or damaging passing vehicles or other objects which might possibly brush against the same. In my discovery there is supplied a much needed and long sought type of *Berberis thunbergii* without the disadvantages of the old brambled type when used for certain purposes where brambles are not desired. The figures of the drawing show a branch of the parent plant in comparison with its thornless progeny.

Referring now more particularly to the origin and chief characteristics of the new variety, the original seedling or bud sport plant was discovered in a block of *Berberis thunbergii* seedlings at Boulder, Colorado, my attention being called thereto by the absence of spines or thorns protruding from the nodes which are an important and the prevailing characteristic in the *Berberis thunbergii*. As previously mentioned, in other respects, the growth of my new variety is identical with the *Berberis thunbergii*, being a hardy, low growing shrub, eighteen to thirty-six inches in height, branches spreading and deeply grooved, slightly lighter brown in color than those of *Berberis thunbergii*, and having no spines.

The leaves are obovate or spatulate, glaucescent beneath, one-half to one and one-half inches long—identical to the leaves of *Berberis thunbergii*, except that the color of the leaves of my thornless variety is more of an intense scarlet than those of *Berberis thunbergii*, and more nearly the color of the *Berberis thunbergii atropurpurea* (red leaved barberry) grown under comparable conditions.

The flowers are yellow in color and identical to those of *Berberis thunbergii* while the fruit is nearly globose and bright red—also identical.

I have found by asexual reproduction that the characteristics of my new variety of thornless barberry are permanent.

Having set forth the most notable features of my invention by comparison with those varieties of the same class which most nearly resemble the same, it is apparent that my thornless barberry is clearly endowed with individual identity and is characterized truly as a new and distinct variety, as manifested particularly by its thornless characteristic and the intense scarlet color of the leaves.

What I claim as new is:—

A new and distinct variety of barberry characterized particularly by the absence of spines and the intense scarlet color of its leaves, as herein shown and described.

In testimony whereof I affix my signature.

WILLIAM GORDON SUTHERLAND.